(12) United States Patent
Haindl

(10) Patent No.: US 7,458,142 B2
(45) Date of Patent: Dec. 2, 2008

(54) METHOD FOR PRODUCING A CANNULA USED SPECIALLY FOR A SPINAL ANAESTHESIA

(76) Inventor: Hans Haindl, Georgsplatz 1, 30974 Wennigsen (DE)

( * ) Notice: Subject to any disclaimer, the term of this patent is extended or adjusted under 35 U.S.C. 154(b) by 761 days.

(21) Appl. No.: 11/108,073

(22) Filed: Apr. 18, 2005

(65) Prior Publication Data

US 2005/0275136 A1 Dec. 15, 2005

Related U.S. Application Data

(63) Continuation of application No. PCT/EP03/010443, filed on Sep. 19, 2003.

(30) Foreign Application Priority Data

Oct. 17, 2002 (DE) .............................. 102 48 377

(51) Int. Cl.
*B29C 59/02* (2006.01)
(52) U.S. Cl. .................... 29/558; 29/557; 604/264; 128/897; 128/898
(58) Field of Classification Search ................ 604/174, 604/175, 164.01, 164.02, 93.01, 264, 263, 604/272, 273, 274, 523; 264/320, 263, 274; 425/224; 128/897, 898; 72/340; 156/196–200, 156/218, 250–254, 211, 267; 29/434, 558, 29/557
See application file for complete search history.

(56) References Cited

U.S. PATENT DOCUMENTS

| | | | | |
|---|---|---|---|---|
| 3,906,932 A | * | 9/1975 | Ayres | 600/577 |
| 4,490,139 A | * | 12/1984 | Huizenga et al. | 604/57 |
| 4,826,492 A | * | 5/1989 | Magasi | 604/274 |
| 4,889,529 A | * | 12/1989 | Haindl | 604/274 |
| 4,922,602 A | * | 5/1990 | Mehl | 29/460 |
| 5,295,980 A | * | 3/1994 | Ersek | 604/272 |
| 5,515,871 A | * | 5/1996 | Bittner et al. | 128/898 |
| 5,848,996 A | | 12/1998 | Eldor | |
| 6,742,236 B1 | * | 6/2004 | Dion et al. | 29/434 |

FOREIGN PATENT DOCUMENTS

| DE | 1 477 025 | 8/1970 |
|---|---|---|
| DE | 34 34 218 A1 | 4/1985 |

(Continued)

OTHER PUBLICATIONS

Office Action from the German Patent and Trademark Office dated Feb. 4, 2003 in German application No. 102 48 377.9-44 filed Oct. 17, 2002 (5 pages).

(Continued)

*Primary Examiner*—Sam Chuan Yao
*Assistant Examiner*—David N Brown, II
(74) *Attorney, Agent, or Firm*—Shlesinger, Arkwright & Garvey LLP

(57) ABSTRACT

Method of producing a cannula used specially for a spinal anesthesia. The cannula is provided with a rigid tube whose distal end comprises a zone or region which gradually tapers in the direction of a puncture or insertion point and a lateral exit orifice or aperture embodied therein. The deformation or bending of an angular zone makes it possible to produce the puncture point and the exit orifice in one stage.

6 Claims, 1 Drawing Sheet

FOREIGN PATENT DOCUMENTS

| | | |
|---|---|---|
| DE | 39 32 014 A1 | 4/1990 |
| DE | 3932014 A1 * | 4/1990 |
| DE | 197 17 253 A1 | 10/1998 |
| DE | 299 08 794 U1 | 7/1999 |
| DE | 199 11 970 A1 | 9/2000 |
| DE | 697 04 908 T2 | 11/2001 |
| EP | 0 271 775 A2 | 6/1988 |
| EP | 1036571 A2 * | 9/2000 |

OTHER PUBLICATIONS

Office Action from the German Patent and Trademark Office dated Jun. 8, 2004 in German application No. 102 48 377.9-44 filed Oct. 17, 2002 (4 pages).

Office Action from the German Patent and Trademark Office dated Aug. 10, 2004 in German application No. 102 48 377.9-44 filed Aug. 10, 2004 (6 pages).

International Search Report dated Jan. 30, 2004 in International Application No. PCT/EP03/10443 filed Sep. 19, 2003 (2 pages).

* cited by examiner

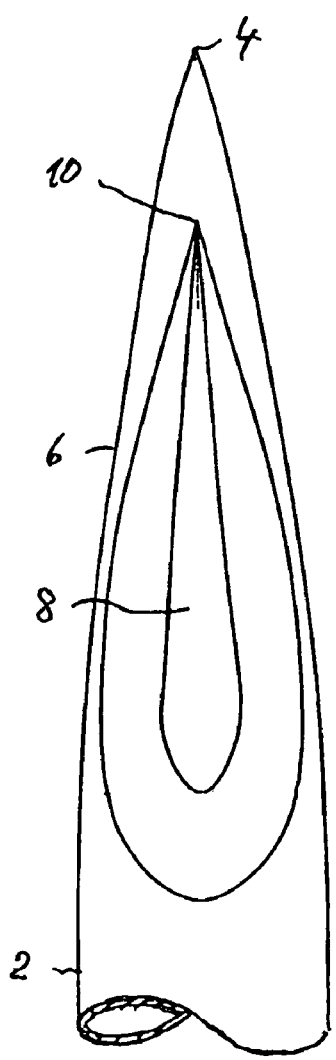
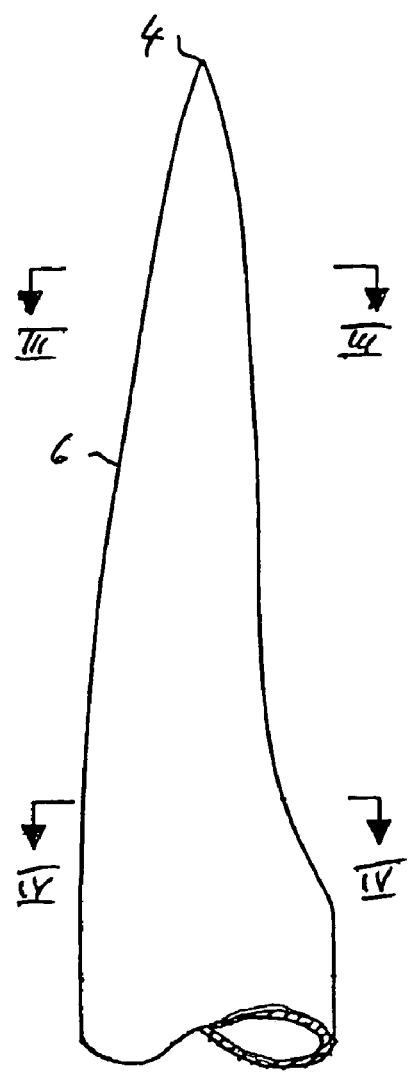
FIG. 1  FIG. 2
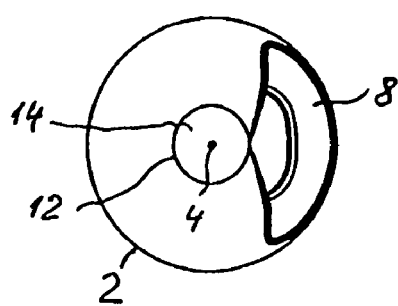
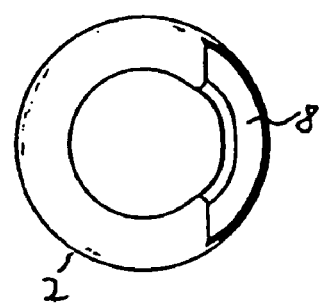
FIG. 3  FIG. 4

METHOD FOR PRODUCING A CANNULA USED SPECIALLY FOR A SPINAL ANAESTHESIA

CROSS REFERENCE TO RELATED APPLICATIONS

This application is a continuation of application Ser. No. PCT/EP2003/010443, filed Sep. 19, 2003, which claims the priority of German application no. 102 48 377.9, filed Oct. 17, 2002, and each of which is incorporated herein by reference.

FIELD OF THE INVENTION

The invention relates to a method for producing a cannula used specifically for spinal anesthesia.

BACKGROUND OF THE INVENTION

From U.S. Pat. No. 5,848,996 a cannula designed for administering spinal anesthesia is known. Said design features a rigid cannula tube, the end of which exhibits a region convexly tapering to an insertion point as well as two outlet apertures forward to where the tapering region begins. This cannula is described a "pencil point spinal cannula" owing to its pencil-point-shaped tip. The disadvantage of this design, however, is its proportionally large distance between the outlet aperture and the insertion point. When spinal anesthesia is administered, this feature requires the cannula to be inserted as deep as possible in the subarachnoid space until the outlet aperture enters the subarachnoid space. Because of the deep insertion required, injuries to the nerve fibers can occur. Because the outlet apertures are round, their cross section can only be small. As a result, fluid exits the outlet aperture at a proportionally high exit velocity. Furthermore, the manufacture of this known cannula is complicated and expensive.

From DE 199 11 970 Al a cannula of the prior art is known. The insertion point is essentially conical and closed. The at least one fluid passage aperture is formed by a longitudinal slit along a side wall of the shaft. The manufacture of the conical point and narrow slit is complicated. Furthermore, the slit acts as an injector, thereby giving exiting fluid a proportionally high velocity, which is not desired. A method for producing this known cannula is not disclosed. Apparently, the conical point is first produced with the narrow slit being subsequently formed in a special stage.

From U.S. Pat. No. 3,906,932 a cannula point for penetrating a container stopper is known, which when introduced into the stopper is not deflected to one side. To achieve this type of function, two diagonal grindings are made on opposite sides of the end of a cylindrical tube. The thereby resulting points are bent toward one another to form a sheath that facilitates easier penetration of a stopper. A cannula of this type is not suited for medical use, since it would not expand pierced tissue, yet would instead penetrate straight through tissue. The process described in this document is therefore not suited for the manufacture of a cannula for medical use.

OBJECTS AND SUMMARY OF THE INVENTION

The object of the invention is to create a process for producing a spinal anesthesia cannula that can be easily performed and yields a cannula with an outlet aperture that features an enlarged cross section and, in particular, is as close as possible to the insertion point.

The invention teaches that this object can be achieved by a method of fabricating a spinal anesthesia cannula, the method comprising the provision of a rigid cannula tube including a cylinder over its entire length, and forming a tapering conical region from the cylindrical cannula tube by tapering the cylindrical cannula tube at a distal end. The cylindrical cannula tube may be chamfered at the distal end of the cannula tube on only one side right to its distal end to produce a chamfered region. The method further including producing edges in the chamfered region during the chamfering of the distal end, and bending the edges together to form and define a substantially conical envelope configured so that the edges touch each other at an outermost distal edge of the chamfered region and thus form an insertion point, but in a region there behind the edges are spaced from each other and thus form an outlet aperture of the cannula adjacent the insertion point.

The process is based on the idea that the outlet aperture should not be made following the deformation of the end of the cannula tube into a convex point as it is in known designs. The invention teaches instead that the distal end of the cannula tube should be formed in such a way prior to deformation as to allow the automatic creation of an outlet aperture during the deformation process. The invention also teaches that to form the conical region from a cylindrical cannula tube the distal end of the cannula tube is preferably chamfered to an outermost distal end.

Naturally this chamfering can have any form. For example, it can be realized as a straight grinding or a convex or concave grinding. Edges formed in the chamfered region are bent together to form and define an essentially conical envelope so that the edges touch each other at the outermost distal edge of the chamfered zone and thereby form an insertion point. Behind the chamfered region, the edges are spaced apart from one another, thereby forming the outlet aperture. By bending together the edges formed through the chamfering to create a conical form, the outlet aperture automatically takes form in a single stage.

In a practical further development of the basic premise of the inventive process, the distal end of the cannula tube is chamfered on two diametrically opposed sides, and paired opposed edges formed in the chamfered zone defining a conical envelope are bent so far together that they touch each other on the outermost distal edge and form a point. In the region behind, however, the edges are spaced apart from one another and thereby form two outlet apertures. In this way, the entire outlet cross section is doubled.

In another further development of this method, the bending together of the edges in the outermost distal zone results in a conical tapering of the cross section so that a closed circumferential surface is formed between the insertion point and the outlet aperture. In this manner the penetration characteristics are improved.

Advantageously the edges of the wall of the cannula tube are rounded in the chamfered zone before being bent together. In this manner, the edges of the outlet aperture will be rounded following deformation. Carrying out the rounding process is known to a person having ordinary skill in the art.

In an embodiment of the inventive method the cannula tube is radially guided during the bending together of the edges. As a result, the deformation in the tapering region is performed symmetrically relative to the elongated imaginary centerline of the cannula tube in such a way that upon completion of the deformation the produced insertion point lies along the centerline.

In executing this embodiment of the method, the shaping, that is, the bending together of the edges in the chamfered region, is preferably facilitated by two shaping jaws moving towards each other in synchronism, whereby the cannula tube is turned relative to the shaping jaws during deformation. As a result the chamfered region exhibits axial symmetry.

An embodiment of the invention is described in further detail below with reference being made to the attached drawings.

Relative terms such as up, down, left, and right are for convenience and are not intended to be limiting.

BRIEF DESCRIPTION OF THE DRAWINGS

FIG. 1 shows the distal end of an embodiment of a cannula produced in accordance with the inventive method with a view of the outlet aperture.

FIG. 2 is a side view from the left of the object illustrated in FIG. 1.

FIG. 3 is a view of section III-III of FIG. 2.

FIG. 4 is a view of section IV-IV of FIG. 2.

DETAILED DESCRIPTION OF THE INVENTION

FIG. 1 shows the cutaway distal end of a cannula tube 2, which includes a tapering region 6 ending at an insertion point 4. Tapering region 6 also features a drop-shaped outlet aperture 8. The apex 10 is adjacent the insertion point 4 and is at a distance from said insertion point 4, so that the outlet aperture 8 thereby ends at a distance from the insertion point 4. As a result, a closed circumferential surface is formed between the insertion point 4 and the apex 10 of the outlet aperture 8. The circumferential surface simplifies insertion into tissue.

FIG. 2 is a side view from the left of the object shown in FIG. 1.

FIG. 3 shows a detail III-III of FIG. 2. The illustration shows a closed circumferential surface 14 marked with a circle 12 extending between the insertion point 4 and outlet aperture 8.

FIG. 4 shows a detail from section IV-IV of FIG. 2. In this illustration, it can be seen that the outlet aperture 8 has a large cross section, so that, in use, a large volume of fluid to can exit the cannula at a low velocity.

The inventive process is described in further detail below with reference being made to FIGS. 1 and 2. The cannula tube 2, which begins as a cylinder extending to an insertion point 4, is chamfered to the insertion point 4 over its entire cross section. This chamfered end is then radially guided between two shaping jaws moving towards each other in synchronism, which are arranged symmetrically along a centerline, which is formed by the elongated imaginary centerline of the cannula tube 2. Cannula tube 2 is rotated while the shaping jaws are moving toward one another in synchronism and thereby against the chamfered end of the cannula tube 2. As a result, the edges formed during chamfering are bent together to form a conical envelope. This deformation step is performed until the closed circumferential surface 14 is formed in the point region and the edges of the chamfered cannula tube move toward one another, so that an outlet aperture 8 is formed therebetween. Prior to the start of the deformation step, the edges of the chamfered end of the cannula tube 2 are rounded, so that the edges of the outlet aperture 8 are rounded following the deformation step, so that when the cannula is inserted into tissue no tissue fragments are cut out.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

The invention claimed is:

1. A method of fabricating a spinal anesthesia cannula, the method comprising:
   a) providing a rigid cannula tube including a 5 cylinder over its entire length;
   b) forming a tapering conical region from the cylindrical cannula tube by tapering the cylindrical cannula tube at a distal end;
   c) chamfering the distal end of the cannula tube on only one side right to its distal end to produce a chamfered region;
   d) producing edges in the chamfered region during the chamfering of the distal end; and
   e) bending the edges together to form and define a substantially conical envelope configured so that the edges touch each other at an outermost distal edge of the chamfered region and thus form an insertion point, but in a region there behind the edges are spaced from each other and thus form an outlet aperture of the cannula adjacent the insertion point.

2. A method as in claim 1, wherein:
   a) the bending of the edges together in the outermost distal region is performed sufficiently so that a closed circumferential surface is formed between the insertion point and the outlet aperture.

3. Method as in claim 1, wherein:
   a) prior to the bending together of the edges, edges of a wall of the cannula tube are rounded in the chamfered region.

4. Method as in claim 1, wherein:
   a) during the bending together of the edges, the cannula tube is radially guided.

5. Method as in claim 4, wherein:
   a) the bending together of the edges is performed symmetrically relative to an imaginary center line of the cannula tube extending in the tapering region, and in such a manner that the insertion point lies on this middle line after the bending together of the edges.

6. Method as in claim 5, wherein:
   a) two shaping jaws are provided; and
   b) the bending together of the edges is performed by the two shaping jaws moving towards each other in synchronism, and by rotating the cannula tube relative to the two shaping jaws during the bending together of the edges.

* * * * *